US012783458B2

(12) United States Patent
Burugapalli et al.

(10) Patent No.: US 12,783,458 B2
(45) Date of Patent: Nov. 3, 2026

(54) SYSTEMS AND METHODS FOR METADATA DRIVEN NORMALIZATION

(71) Applicant: Truveta Inc., Bellevue, WA (US)

(72) Inventors: Srinivasa R. Burugapalli, Sammamish, WA (US); Ramesh Kolavennu, Sammamish, WA (US); Wing Tsui, Bellevue, WA (US); Patricia Cuplin, Brier, WA (US); Mehrdad Biglari, Sammamish, WA (US)

(73) Assignee: Truveta Inc., Bellevue, WA (US)

( * ) Notice: Subject to any disclaimer, the term of this patent is extended or adjusted under 35 U.S.C. 154(b) by 37 days.

(21) Appl. No.: 18/647,619

(22) Filed: Apr. 26, 2024

(65) Prior Publication Data

US 2024/0370404 A1 Nov. 7, 2024

Related U.S. Application Data

(60) Provisional application No. 63/499,533, filed on May 2, 2023.

(51) Int. Cl.
*G06F 16/10* (2019.01)
*G06F 16/11* (2019.01)
*G16H 10/60* (2018.01)

(52) U.S. Cl.
CPC ........... *G06F 16/116* (2019.01); *G16H 10/60* (2018.01)

(58) Field of Classification Search
CPC .............................. G06F 16/116; G16H 10/60
See application file for complete search history.

(56) References Cited

U.S. PATENT DOCUMENTS

| | | | | |
|---|---|---|---|---|
| 7,428,494 | B2 | 9/2008 | Hasan et al. | |
| 7,827,234 | B2 | 11/2010 | Eisenberger et al. | |
| 10,534,816 | B2 | 1/2020 | Gilder et al. | |
| 10,657,613 | B2 | 5/2020 | Bucur et al. | |
| 11,151,125 | B1 * | 10/2021 | Dwivedi | G06F 11/3409 |
| 11,295,867 | B2 | 4/2022 | Oliveira et al. | |

(Continued)

FOREIGN PATENT DOCUMENTS

| | | |
|---|---|---|
| CA | 2418239 C | 5/2014 |
| CN | 101194255 B | 6/2011 |

(Continued)

OTHER PUBLICATIONS

Bodenreider et al., Comparing the Representation of Anatomy in the FMA and Snomed CT, Amia 2006 Symposium Proceeding, pp. 46-50.

(Continued)

*Primary Examiner* — Daniel A Kuddus
(74) *Attorney, Agent, or Firm* — Workman Nydegger

(57) ABSTRACT

Techniques for metadata driven normalization are disclosed. In some examples, the disclosed technology includes receiving a plurality of configuration data structures, each configuration data structure comprising one or more mappings, each mapping comprising a reference to instructions for transforming data. Metadata associated with a received data set is identified and compared to metadata information associated with the configuration data structures. A configuration data structure is selected based on this comparison and referenced instructions are used to generate and then execute code for transforming the received data set.

19 Claims, 11 Drawing Sheets

(56) References Cited

U.S. PATENT DOCUMENTS

| | | | | |
|---|---|---|---|---|
| 12,057,208 | B1 | 8/2024 | Esman | |
| 12,086,287 | B2 | 9/2024 | Jensen et al. | |
| 12,475,257 | B2 | 11/2025 | Papel et al. | |
| 2008/0306872 | A1 | 12/2008 | Felsher | |
| 2009/0030290 | A1 | 1/2009 | Kozuch et al. | |
| 2010/0077006 | A1 | 3/2010 | El et al. | |
| 2012/0046969 | A1 | 2/2012 | Schoenberg | |
| 2014/0257045 | A1 | 9/2014 | Hu et al. | |
| 2014/0330578 | A1 | 11/2014 | Pincus | |
| 2016/0147945 | A1 | 5/2016 | Maccarthy et al. | |
| 2016/0154978 | A1 * | 6/2016 | Baker | G06F 16/285 726/26 |
| 2016/0210427 | A1 | 7/2016 | Mynhier et al. | |
| 2017/0103232 | A1 * | 4/2017 | Scaiano | G16H 10/60 |
| 2017/0161439 | A1 | 6/2017 | Raduchel et al. | |
| 2018/0089382 | A1 * | 3/2018 | Allen | G06F 40/205 |
| 2018/0158552 | A1 | 6/2018 | Liu et al. | |
| 2018/0322946 | A1 | 11/2018 | Ika et al. | |
| 2019/0034590 | A1 | 1/2019 | Oren et al. | |
| 2019/0034591 | A1 | 1/2019 | Mossin et al. | |
| 2019/0057774 | A1 * | 2/2019 | Velez | G16H 50/20 |
| 2019/0095478 | A1 * | 3/2019 | Tankersley | G06F 11/30 |
| 2019/0371475 | A1 | 12/2019 | Oliveira et al. | |
| 2020/0176098 | A1 * | 6/2020 | Lucas | G16H 10/60 |
| 2020/0276098 | A1 | 9/2020 | Nabi et al. | |
| 2022/0129584 | A1 | 4/2022 | Blackport et al. | |
| 2022/0171747 | A1 | 6/2022 | Rajyaguru et al. | |
| 2022/0222374 | A1 | 7/2022 | Antoniou et al. | |
| 2023/0144503 | A1 | 5/2023 | Powers et al. | |
| 2023/0147366 | A1 | 5/2023 | Marcjan et al. | |
| 2023/0148326 | A1 | 5/2023 | Papel et al. | |
| 2023/0162825 | A1 | 5/2023 | Nanduri et al. | |
| 2024/0087687 | A1 | 3/2024 | Marcjan et al. | |
| 2024/0412830 | A1 | 12/2024 | Marcjan et al. | |
| 2025/0232063 | A1 | 7/2025 | Shinn et al. | |

FOREIGN PATENT DOCUMENTS

| | | | |
|---|---|---|---|
| EP | 1994484 | B1 | 3/2015 |
| WO | WO2007084502 | A1 * | 7/2007 |
| WO | 2023081912 | A1 | 5/2023 |
| WO | 2023081919 | A1 | 5/2023 |
| WO | 2023081921 | A1 | 5/2023 |
| WO | WO2023081909 | A1 * | 5/2023 |

OTHER PUBLICATIONS

Devlin, Jacob et al., BERT: Pre-training of Deep Bidirectional Transformers for Language Understanding, Proceedings of NAACL-HLT 2019, pp. 4171-4186.
International Search Report and Written Opinion mailed Feb. 27, 2023, International Application No. PCT/US2022/079455, 19 pages.
International Search Report and Written Opinion mailed Mar. 9, 2023, International Application No. PCT/US2022/079446, 12 pages.
International Search Report and Written Opinion mailed Mar. 13, 2023, International Application No. PCT/US2022/079476, 13 pages.
International Search Report and Written Opinion mailed Mar. 28, 2023, International Application No. PCT/US2022/079474, 21 pages.
Jimenez-Ruiz et al., Logic-based assessment of the compatibility of UMLS ontology sources, Journal of Biomedical Semantics, 2011, 2(Suppl 1): S2.
Luong et al., Multi-Task Sequence To Sequence Learning, published as a conference paper at ICLR, 2016, 10 pages.
Xue, Linting et al., ByT5: Towards a Token-Free Future with Pre-trained Byte-to-Byte Models, endeavarXiv:2105.13626v3 [cs. CL] Mar. 8, 2022, 16 pages.
Xue, Linting et al., mT5: A Massively Multilingual Pre-trained Text-to-Text Transformer, arXiv:2010.11934v3 [cs.CL] Mar. 11, 2021, 17 pages.
Ahmad, Arab , et al., "MDMP: A new algorithm to create inverted index files in BigData, using MapReduce", 2017 7th International Conference On Computer and Knowledge Engineering (ICCKE), IEEE, Oct. 26, 2017 (Oct. 26, 2017), pp. 372-378.
Garfinkel, Simson L., "De-identification of personal information NIST IR 8053", NIST, National Institute of Standards and Technology (NIST) Oct. 21, 2015 (Oct. 21, 2015), pp. 1-54, XP061056032, DOI: 10.6028/NIST.IR.8053.
Sweeney, Latanya , "k-anonymity: a model for protecting privacy k-Anonymity: A Model for Protecting Privacy 1", International Journal on Uncertainty, Oct. 31, 2002 (Oct. 31, 2002), pp. 557-570, XP055268614, Retrieved from the Internet: URL:https://epic.org/privacy/reidentificat ion/Sweeney Article. pdf [retrieved on Apr. 26, 2016].
Taneja, Himanshu , et al., "Preserving Privacy of Patients Based on Re-identification Risk", Procedia Computer Science, Elsevier, Amsterdam, NL, vol. 70, 21 November 201 Nov. 21, 2015), pp. 448-454, XP029309606, ISSN: 187.7-0509, DOI: 10.1016/J.PROCS.2015.10.073.
Uwe, Roth , "A Generalized View on Pseudonyms and Domain Specific Local Identifiers. Lessons Learned from Various Use Cases", The International Journal On Advances in Security, vol. 7, No. 3-4, Dec. 31, 2014 (Dec. 31, 2014, pp. 76-92, XP093019165, ISSN: 1942-2636.

* cited by examiner

INPUT VALUES

| Diagnosis |
|---|
| Hypercoagulable state associated with COVID-19 (HCC) |
| Hypercoagulable state associated with severe acute respiratory syndrome coronavirus 2 (SARS-CoV-2) infection (HCC) |

⇨

NORMALIZED VALUES

| SNOMED CT Concept | SNOMED CT Code | Confidence Score |
|---|---|---|
| Hypercoagulability state | 76612001 | .98 |
| Disease caused by severe acute respiratory syndrome coronavirus 2 | 840539006 | .94 |

FIG. 4

SYSTEMS AND METHODS FOR METADATA DRIVEN NORMALIZATION

CROSS-REFERENCE TO RELATED APPLICATIONS

This application claims the benefit of priority to U.S. Patent Application No. 63/499,533, filed May 2, 2024, which is incorporated herein by reference in its entirety.

This application is related to the following applications, each of which is hereby incorporated by reference in its entirety: U.S. Provisional Patent Application No. 63/263,735, entitled "SYSTEMS AND METHODS FOR DATA NORMALIZATION," filed on Nov. 8, 2021, U.S. Provisional Patent Application No. 63/263,725, entitled HEALTH DATA PLATFORM AND ASSOCIATED METHODS, filed on Nov. 8, 2021, U.S. Provisional Patent Application No. 63/263,733, entitled "SYSTEMS AND METHODS FOR INDEXING AND SEARCHING HEALTH DATA," filed on Nov. 8, 2021, U.S. Provisional Patent Application No. 63/263,731, entitled "SYSTEMS AND METHODS FOR DE-IDENTIFYING PATIENT DATA," filed on Nov. 8, 2021, U.S. Provisional Patent Application No. 63/268,995, entitled "SYSTEMS AND METHODS FOR INDEXING AND SEARCHING HEALTH DATA," filed on Mar. 8, 2022, U.S. Provisional Patent Application No. 63/268,993, entitled "SYSTEMS AND METHODS FOR QUERYING HEALTH DATA," filed on Mar. 8, 2022, U.S. patent application Ser. No. 18/053,504, entitled "HEALTH DATA PLATFORM AND ASSOCIATED METHODS," filed on Nov. 8, 2022, U.S. patent application Ser. No. 18/053,540, entitled "SYSTEMS AND METHODS FOR INDEXING AND SEARCHING HEALTH DATA," filed on Nov. 8, 2022, U.S. patent application Ser. No. 18/053,643, entitled "SYSTEMS AND METHODS FOR DE-IDENTIFYING PATIENT DATA," filed on Nov. 8, 2022, and U.S. patent application Ser. No. 18/053,654 entitled "SYSTEMS AND METHODS FOR DATA NORMALIZATION," filed on Nov. 8, 2022.

TECHNICAL FIELD

The present technology generally relates to healthcare, and in particular, to systems and methods for data normalization.

BACKGROUND

Medical research has come a long way since paper records were digitized. Researchers now have access to more health data than ever before. But limitations persist. Research is still often conducted on relatively small data sets that may be weeks or even months old and may not represent the full diversity of a population. This can result in biased insights that can compromise patient care.

Healthcare entities such as hospitals, clinics, and laboratories produce enormous volumes of health data. This health data can provide valuable insights for research and improving patient care. However, the patient records and other health data received from health system members can arrive from different databases in multiple formats, often incorporating a wide variety of terminologies and medical code sets. The structure of these records can also vary widely. Additionally, even with standard medical terminology, the way in which that terminology is used can also vary widely. A heart attack in one record, for example, may be described as acute myocardial infarction or AMI in another. All of these different structures, terminologies, and semantics can make it difficult to work across heath data records and identify meaningful trends and insights. There has been much progress made to arrive at a set of standards and processes that can help address this inconsistency, but the larger and more diverse the dataset, the more complex and time consuming the processing.

The HIPAA Privacy Rule does not restrict the use or disclosure of de-identified health information-health information that neither identifies nor provides a reasonable basis for identifying a patient or individual. However, conventional techniques for de-identifying health data may remove too much information from the patient record, resulting in data that has limited utility for subsequent applications. Additionally, conventional de-identification techniques may not be well-suited for handling patient data that is received at different times or from different health systems because, for example, they are not stored in a uniform format. Accordingly, improved systems and methods for de-identifying patient data are needed.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 4 illustrates an example of mapping diagnoses to standard SNOMED CT concepts, in accordance with embodiments of the present technology.

DETAILED DESCRIPTION

Figure 1A:
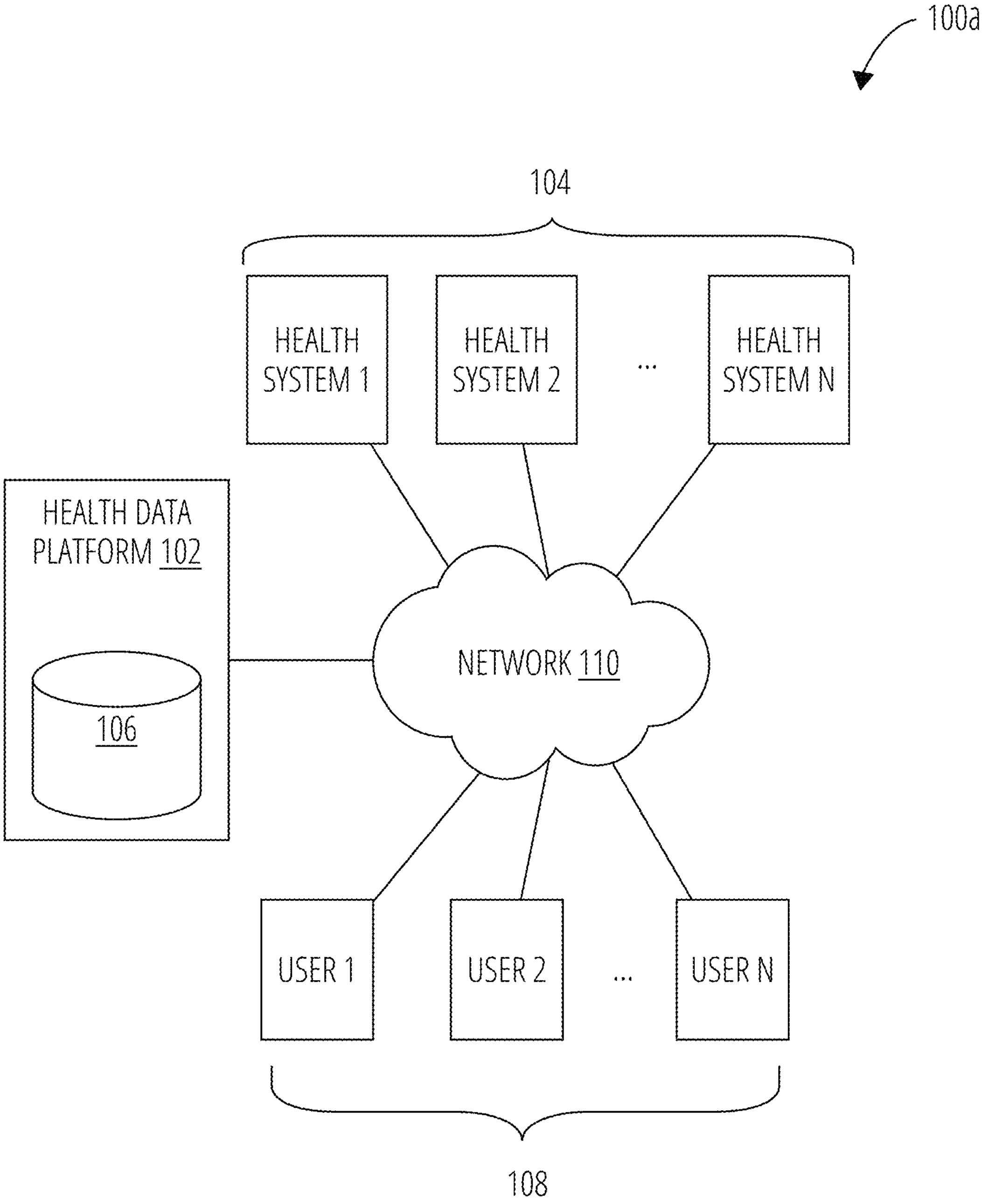
FIG. 1A is a schematic diagram of a computing environment in which a health data platform can operate, in accordance with embodiments of the present technology.

The present technology relates to systems and methods for data normalization. In some embodiments, a health data platform is configured to consolidate multiple and disparate data streams into a common data model for effective research. For example, the health data platform can interface with health system members providing more than 16% of care in the United States in tens of thousands of clinical care sites in 42 states, representing the full diversity of the country across age, geography, race, ethnicity, and gender. Billions of clinical data points from this care can be brought together in the health data platform to enable research on any drug, disease, or device across the full diversity of the United States. The health data platform can assemble millions of patient records from multiple health provider members. In some embodiments, data flows into the system daily, providing researchers with virtually real time updates. However, the speed, volume, and diversity of this data can pose significant management challenges. For example, the data received from the health system members can include all Electronic Health Record (EHR) data, such as labs, vitals, diagnosis codes, procedure codes, physician notes, imaging reports, pathology reports, images, and/or genomics information. The structure of these records can vary widely, as well as the terminology used in the records. Accordingly, there is a need for systems and methods that can make sense of a large and diverse flow of health data without compromising the diversity and accuracy of that data, or the speed of its delivery for research and/or other purposes.

The present technology provides a process for making data useful from health system members, referred to herein as "normalization." Data normalization can refer to the practice of converting a diverse flow of data into a unified and consistent data model. This can include two different aspects: semantic normalization and syntactic (schema) normalization. Semantic normalization involves converting concepts or terms into a standard format. Conventionally, the task of interpreting health data and mapping to standard models is done by an expert team of annotators, informaticists, and other clinical experts. Syntactic (schema) normalization involves converting one data model into another data model. Conventionally, this task has been performed by data analysts and data engineers writing custom code for each transformation. Given the size and speed of the data flow that health data platform manages, these processes are not practical or scalable. Instead, the present technology provides a unique system that combines artificial intelligence (AI), machine learning, and natural language processing with expert analysis. In this way, the present technology can automate much of the normalization process at massive scale while leveraging clinical experts to monitor, update and evolve the system.

The present technology further includes techniques for further automating the process of normalization through metadata driven normalization, which allows data administrators to store references to instructions for normalizing data, which can be retrieved when new data is received and applied to the data. Automating the normalization process both speeds up the process of data normalization and reduces errors that may be introduced through the process of normalization, thereby reducing the load on resources and improving the quality of the normalized data.

In some embodiments, the disclosed techniques provide a network-based patient data management method that acquires, aggregates, and normalizes patient information from various sources into a uniform or standardized format, stores the aggregated patient information, and notifies health care providers and/or patients after information is updated via one or more communication channels. In some cases, the acquired patient information may be provided by one or more users through an interface, such as a graphical user interface, that provides remote access to users over a network so that any one or more of the users can provide at least one updated patient record in real time, such as a patient record in a format other than the uniform or standardized format, including formats that are dependent on a hardware and/or software platform used by a user providing the patient information.

In some embodiments, the disclosed techniques employ a data catalog that facilitates data governance and analyzing and adding records to a repository. The data catalog captures metadata for multi-modal data, thereby providing a single place to track data in the system. Furthermore, metadata driven transforms provide for data normalization that allows data modelers and analysts to work independent of target data platform where data is processed. Metadata driven processing improves consistency, debugging and reduces maintenance while capturing data lineage. Metrics and alerts related to any data and quality of data can be authored and persisted in data catalog while schema and transforms can be versioned, ensuring backward compatibility.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The headings provided herein are for convenience only and do not interpret the scope or meaning of the claimed present technology. Embodiments under any one heading may be used in conjunction with embodiments under any other heading.

I. Health Data Platform

Figure 1B:
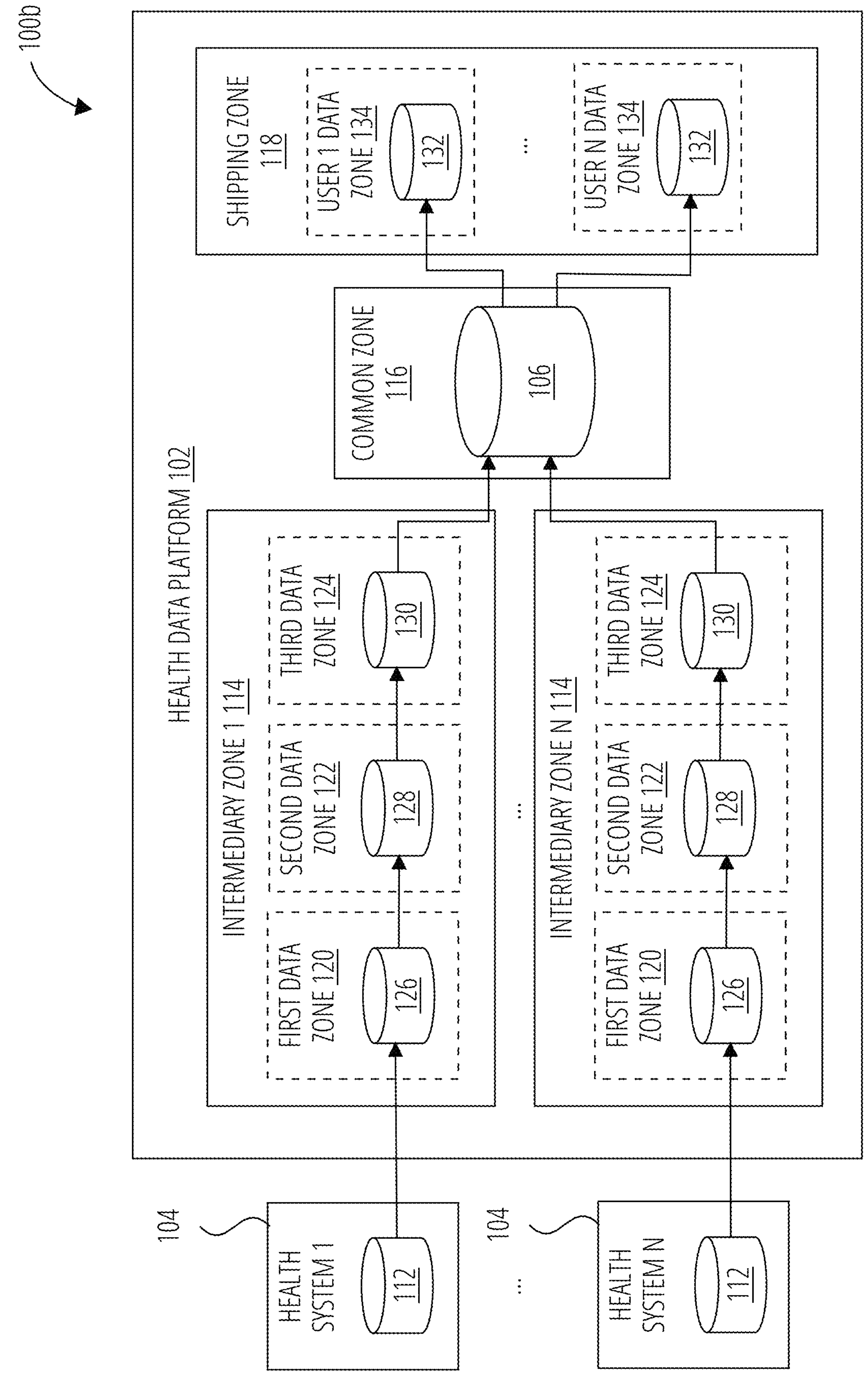
FIG. 1B is a schematic diagram of a data architecture that can be implemented by a health data platform, in accordance with embodiments of the present technology.

FIGS. 1A and 1B provide a general overview of a health data platform configured in accordance with embodiments of the present technology. Specifically, FIG. 1A is a schematic diagram of a computing environment 100*a* in which a health data platform 102 can operate, and FIG. 1B is a schematic diagram of a data architecture 100*b* that can be implemented by the health data platform 102.

Referring first to FIG. 1A, the health data platform 102 is configured to receive health data from a plurality of health systems 104, aggregate the health data into a common data repository 106, and allow one or more users 108 to access the health data stored in the common data repository 106. As described in further detail below, the common data repository 106 can store health data from multiple different health systems 104 and/or other data sources in a uniform schema, thus allowing for rapid and convenient searching, analytics, modeling, and/or other applications that would benefit from access to large volumes of health data.

The health data platform 102 can be implemented by one or more computing systems or devices having software and hardware components (e.g., processors, memory) configured to perform the various operations described herein. For example, the health data platform 102 can be implemented as a distributed "cloud" server across any suitable combination of hardware and/or virtual computing resources. The health data platform 102 can communicate with the health system 104 and/or the users 108 via a network 110. The network 110 can be or include one or more communications networks, such as any of the following: a wired network, a wireless network, a metropolitan area network (MAN), a local area network (LAN), a wide area network (WAN), a virtual local area network (VLAN), an internet, an extranet, an intranet, and/or any other suitable type of network or combinations thereof.

The health data platform 102 can be configured to receive and process many different types of health data, such as patient data. Examples of patient data include, but are not limited to, any of the following: age, gender, height, weight, demographics, symptoms (e.g., types and dates of symptoms), diagnoses (e.g., types of diseases or conditions, date of diagnosis), medications (e.g., type, formulation, prescribed dose, actual dose taken, timing, dispensation records), treatment history (e.g., types and dates of treatment procedures, the healthcare facility or provider that administered the treatment), vitals (e.g., body temperature, pulse rate, respiration rate, blood pressure), laboratory measurements (e.g., complete blood count, metabolic panel, lipid panel, thyroid panel, disease biomarker levels), test results (e.g., biopsy results, microbiology culture results), genetic data, diagnostic imaging data (e.g., X-ray, ultrasound, MRI, CT), clinical notes and/or observations, other medical history (e.g., immunization records, death records), insurance information, personal information (e.g., name, date of birth, social security number (SSN), address), familial medical history, and/or any other suitable data relevant to a patient's health. In some embodiments, the patient data is provided in the form of electronic health record (EHR) data, such as structured EHR data (e.g., schematized tables representing orders, results, problem lists, procedures, observations, vitals, microbiology, death records, pharmacy dispensation records, lab values, medications, allergies, etc.) and/or unstructured EHR data (e.g., patient records including clinical notes, pathology reports, imaging reports, etc.). A set of patient data relating to the health of an individual patient may be referred to herein as a "patient record."

The health data platform 102 can receive and process patient data for an extremely large number of patients, such as thousands, tens of thousands, hundreds of thousands, millions, tens of millions, or hundreds of millions of patients. The patient data can be received continuously, at predetermined intervals (e.g., hourly, daily, weekly, monthly), when updated patient data is available and/or pushed to the health data platform 102, in response to requests sent by the health data platform 102, or suitable combinations thereof. Thus, due to the volume and complexity of the patient data involved, many of the operations performed by the health data platform 102 are impractical or impossible for manual implementation.

Optionally, the health data platform 102 can also receive and process other types of health data. For example, the health data can also include facility and provider information (e.g., names and locations of healthcare facilities and/or providers), performance metrics for facilities and providers (e.g., bed utilization, complication rates, mortality rates, patient satisfaction), hospital formularies, health insurance claims data (e.g., 835 claims, 837 claims), supply chain data (e.g., information regarding suppliers of medical devices and/or medications), device data (e.g., device settings, indications for use, manufacturer information, safety data), health information exchanges and patient registries (e.g., immunization registries, disease registries), research data, regulatory data, and/or any other suitable data relevant to healthcare. The additional health data can be received continuously, at predetermined intervals (e.g., hourly, daily, weekly, monthly), as updated data is available, upon request by the health data platform 102, or suitable combinations thereof.

The health data platform 102 can receive patient data and/or other health data from one or more health systems 104. Each health system 104 can be an organization, entity, institution, etc., that provides healthcare services to patients. A health system 104 can optionally be composed of a plurality of smaller administrative units (e.g., hospitals, clinics, labs, or groupings thereof), also referred to herein as "care sites." The health data platform 102 can receive data from any suitable number of health systems 104, such as one, two, four, five, ten, fifteen, twenty, thirty, forty, fifty, hundreds, thousands, or more different health systems 104. Each health system 104 can include or otherwise be associated with at least one computing system or device (e.g., a server) that communicates with the health data platform 102 to transmit health data thereto. For example, each health system 104 can generate patient data for patients receiving services from the respective health system 104, and can transmit the patient data to the health data platform 102. As another example, each health system 104 can generate operational data relating to the performance metrics of the care sites within the respective health system 104, and can transmit the operational data to the health data platform 102.

Optionally, the health data platform 102 can receive health data from other data sources besides the health systems 104. For example, the health data platform 102 can receive health data from one or more databases, such as public or licensed databases on drugs, diseases, medical ontologies, demographics and/or other patient data, etc. (e.g., SNOMED CT, RxNorm, ICD-10, FHIR, LOINC, UMLS, OMOP, LexisNexis, state vaccine registries). In some embodiments, this additional health data provides metadata that is used to process, analyze, and/or enhance patient data received from the health systems 104, as described below.

The health data platform 102 can perform various data processing operations on the received health data, such as de-identifying health data that includes patient identifiers, converting the health data from a health system-specific format into a uniform format, and/or enhancing the health data with additional data. Subsequently, the health data platform 102 can aggregate the processed health data in the common data repository 106. The common data repository 106 can be or include one or more databases configured to store health data from multiple health systems 104 and/or other data sources. The health data in the common data repository 106 can be in a uniform schema or format to facilitate downstream applications. For example, the health data platform 102 performs additional data processing operations on the health data in the common data repository 106, such as analyzing the health data (e.g., using machine learning models and/or other techniques), indexing or otherwise preparing the health data for search and/or other applications, updating the health data as additional data is received, and/or preparing the health data for access by third parties (e.g., by performing further de-identification processes). Additional details of some of the operations that can be performed by the health data platform 102 are described below with respect to FIG. 1B.

The health data platform 102 can allow one or more users 108 (e.g., researchers, healthcare professionals, health system administrators) to access the aggregated health data stored in the common data repository 106. Each user 108 can communicate with the health data platform 102 via a computing device (e.g., personal computer, laptop, mobile device, tablet computer) and the network 110. For example, a user 108 can send a request to the health data platform 102 to retrieve a desired data set, such as data for a population of patients meeting one or more conditions (e.g., diagnosed with a particular disease, receiving particular medication, belonging to a particular demographic group). The health data platform 102 can search the common data repository 106 to identify a subset of the stored health data that fulfills the requested conditions, and can provide the identified subset to the user 108. Optionally, the health data platform 102 can perform additional operations on the identified subset of health data before providing the data to the user, such as de-identification and/or other processes to ensure data security and patient privacy protection.

FIG. 1B illustrates the data architecture 100*b* of the health data platform 102, in accordance with embodiments of the present technology. The health data platform 102 can be subdivided into a plurality of discrete data handling zones, also referred to herein as "zones" or "domains." Each zone is configured to perform specified data processing operations and store the data resulting from such operations. For example, in the illustrated embodiment, the health data platform 102 includes a plurality of intermediary zones 114 (also known as "embassies") that receive and process health data from the health systems 104, a common zone 116 that aggregates the data from the intermediary zones 114 in the common data repository 106, and a shipping zone 118 that provides selected data for user access. Each zone can include access controls, security policies, privacy rules, and/or other measures that define data isolation boundaries tailored to the sensitivity level of the data contained within that zone. The flow of data between zones can also be strictly controlled to mitigate the risk of privacy breaches and/or other data security risks.

In the illustrated embodiment, each of the health systems 104 includes at least one health system database 112. The health system database 112 can store health data produced by the respective health system 104, such as patient data for the patients receiving healthcare services from the health system 104, operational data for the health system 104, etc. The patient data stored in the health system database 112 can include or be associated with identifiers such as the patient's name, address (e.g., street address, city, county, zip code), relevant dates (e.g., date of birth, date of death, admission date, discharge date), phone number, fax number, email address, SSN, medical record number, health insurance beneficiary number, account number, certificate or license number, vehicle identifiers and/or serial numbers (e.g., license plate numbers), device identifiers and/or serial numbers, web URL, IP address, finger and/or voice prints, photographic images, and/or any other characteristic or information that could uniquely identify the patient. Accordingly, the patient data can be considered to be PHI (e.g., electronic PHI (ePHI)), which may be subject to strict regulations on disclosure and use.

As shown in FIG. 1B, health data can be transmitted from the health systems 104 to the health data platform 102 via respective secure channels and/or over a communications network (e.g., the network 110 of FIG. 1A). The health data can be transmitted continuously, at predetermined intervals, in response to pull requests from the health data platform 102, when the health systems 104 push data to the health data platform 102, or suitable combinations thereof. For example, some or all of the health systems 104 can provide a daily feed of data to the health data platform 102.

The health data from the health systems 104 can be received by the intermediary zones 114 of the health data platform 102. In some embodiments, the intermediary zones 114 are configured to process the health data from the health systems 104 to prepare the data for aggregation in the common zone 116. For example, each intermediary zone 114 can de-identify the received health data to remove or otherwise obfuscate identifying information so that the health data is no longer classified as PHI and can therefore be aggregated and used in a wide variety of downstream applications (e.g., search, analysis, modeling). The intermediary zone 114 can also normalize the received health data by converting the data from a health system-specific format to a uniform format suitable for aggregation with health data from other health systems 104. As shown in FIG. 1B, each intermediary zone 114 can receive health data from a single respective health system 104. The intermediary zones 114 can be isolated from each other such that health data across different health systems 104 cannot be combined with each other or accessed by unauthorized entities (e.g., a health system 104 other than the health system 104 that originated the data) before patient identifiers have been removed.

In the illustrated embodiment, each intermediary zone 114 includes a plurality of data zones that sequentially process the health data from the respective health system 104. For example, in the illustrated embodiment, each intermediary zone 114 includes a first data zone 120 (also known as a "landing zone"), a second data zone 122 (also known as an "enhanced PHI zone"), and a third data zone 124 (also known as an "enhanced DeID zone").

As shown in FIG. 1B, the health data from each health system 104 can initially be received and processed by the first data zone 120 (landing zone). The first data zone 120 can implement one or more data ingestion processes to extract relevant data and/or filter out erroneous or irrelevant data. The data ingestion processes can be customized based on the particular health system 104, such as based on the data types and/or formats produced by the health system 104. Accordingly, the first data zones 120 within different intermediary zones 114 can implement different data ingestion processes, depending on the particular data output of the corresponding health system 104. The data resulting from the data ingestion processes can be stored in a first database 126 within the first data zone 120. The data can remain in the first database 126 indefinitely or for a limited period of time (e.g., no more than 30 days, no more than 1 year, etc.), e.g., based on the preferences of the respective health system 104, security considerations, and/or other factors. The data in the first database 126 can still be considered PHI because the patient identifiers have not yet been removed from the data. Accordingly, the first data zone 120 can be subject to relatively stringent access controls and data security measures.

The data produced by the first data zone 120 can be transferred to the second data zone 122 (enhanced PHI zone). In some embodiments, the data received from the first data zone 120 is initially in a non-uniform format, such as a format specific to the health system 104 that provided the data. Accordingly, the second data zone 122 can implement one or more data normalization processes to convert the data into a unified, normalized format or schema (e.g., a standardized data model). Optionally, data normalization can include enhancing, enriching, annotating, or otherwise supplementing the health data with additional data (e.g., health metadata received from databases and/or other data sources). Additional details of the data normalization processes disclosed herein are provided in Section II below. The data resulting from these processes can be stored in a second database 128 within the second data zone 122. The data can remain in the second database 128 indefinitely or for a limited period of time (e.g., no more than 30 days, 1 year, etc.), e.g., based on the preferences of the respective health system 104, security considerations, and/or other factors. The data stored in the second database 128 can still be considered PHI because the patient identifiers have not yet been removed from the data. Accordingly, the second data zone 122 can also be subject to relatively stringent access controls and data security measures, similar to the first data zone 120.

The data produced by the second data zone 122 can be transferred to the third data zone 124 (enhanced DeID zone). The third data zone 124 can implement one or more de-identification processes to remove and/or modify identifiers from the data so that the data is no longer classified as PHI. The de-identification processes can include, for example, modifying the data to remove, alter, coarsen, group, and/or shred patient identifiers, and/or removing or suppressing certain patient records altogether. For example, a patient record can be suppressed if the record would still potentially be identifiable even after the identifiers have been removed and/or modified (e.g., if the record shows a diagnosis of an extremely rare disease). In some embodiments, the de-identification processes also include producing tokens that allow data from the same patient to be tracked without using the original identifiers. The resulting de-identified data can be stored in a third database 130 within the third data zone 124. The data can remain in the third database 130 indefinitely or for a limited period of time (e.g., no more than 30 days, 1 year, etc.), e.g., based on the preferences of the respective health system 104, security considerations, and/or other factors. Because the data stored in the third database 130 is no longer considered PHI, the third data zone 124 can have less stringent access controls and data security measures than the first and second data zones 120, 122.

The de-identified data produced by each intermediary zone 114 can be transferred to a common zone 116 within the health data platform 102 via respective secure channels. The common zone 116 can include the common data repository 106 that stores aggregated health data from all of the health systems 104. As discussed above, the data stored in the common data repository 106 has been de-identified and/or normalized into a uniform schema, and can therefore be used in many different types of downstream applications. For example, the common zone 116 can implement processes that analyze the data in the common data repository 106 using machine learning and/or other techniques to produce various statistics, analytics (e.g., cohort analytics, time series analytics), models, knowledge graphs, etc. As another example, the common zone 116 can implement processes that index the data in the common data repository 106 to facilitate search operations.

The data stored in the common data repository 106 can be selectively transferred to the shipping zone 118 of the health data platform 102 for access by one or more users 108 (not shown in FIG. 1B). In the illustrated embodiment, the shipping zone 118 includes a plurality of user data zones 134. Each user data zone 134 can be customized for a particular user 108, and can store and expose a selected subset of data for access by that user 108. The user data zones 134 can be isolated from each other so that each user 108 can only access data within their assigned user data zone 134. The amount, type, and/or frequency of data transferred to each user data zone 134 can vary depending on the data requested by the user 108 and the risk profile of the user 108. For example, the user 108 can send a request to the health data platform 102 (e.g., via the network 110 of FIG. 1A) for access to certain data in the common data repository 106 (e.g., data for patients who have been diagnosed with a particular disease, belong to a particular population, have received a particular treatment procedure, etc.). The common zone 116 can implement a search process to identify a subset of the data in the common data repository 106 that fulfills the request parameters. Optionally, depending on the risk profile of the user 108, the common zone 116 can perform additional de-identification processes and/or apply other security measures to the identified data subset. The identified data subset can then be transferred to the user data zone 134 for access by the user 108 (e.g., via a secure channel in the network 110 of FIG. 1A).

The data architecture **100*b* illustrated in FIG. 1B can be configured in many different ways. For example, although the intermediary zones 114 are illustrated in FIG. 1B as having three data zones, in other embodiments, some or all of the intermediary zones 114 can include fewer or more data zones. Any of the zones illustrated in FIG. 1**B can alternatively be combined with each other into a single zone, or can be subdivided into multiple zones. Any of the processes described herein as being implemented by a particular zone can instead be implemented by a different zone, or can be omitted altogether.

II. Data Normalization

The present technology provides various types of normalization for effective processing of health data. Syntactic normalization addresses structural differences in records. Semantic normalization addresses variances in terminology within that structure.

With syntactic normalization, similar fields used in electronic health records are mapped to a common schema. A patient's birth date, for example, might be in a field marked BirthDate in one record and DOB in another. The health data platform can create one field that applies to both and add this field to the common schema model. The innovative mapping application can automatically move huge volumes of data into the schema. The schema mapping can be informed by leading standards such as Fast Healthcare Interoperability Resources (FHIR®). Additionally, the health data platform can continually add to the schema model to accommodate data with unique structures while also maintaining as much uniformity across records as possible.

Figure 2:
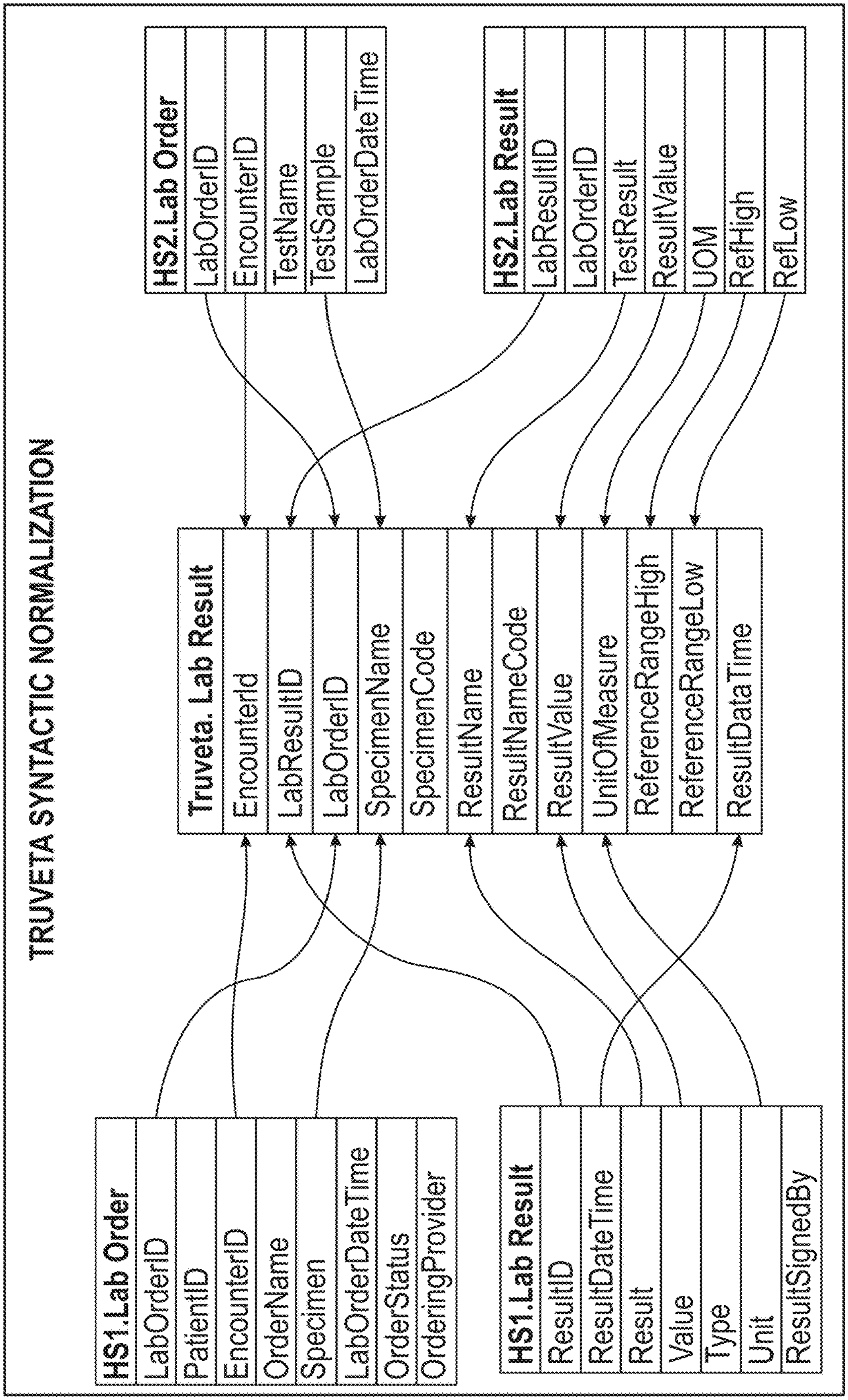
FIG. 2 illustrates an example of syntactic normalization, in accordance with embodiments of the present technology.

FIG. 2 illustrates an example showing how syntactic normalization is done for datasets from two health system members. In some cases, there are identical fields (e.g., LabOrderID) which are mapped directly to the model. In other cases, a new field is created (e.g., SpecimenName) that covers several, similarly named fields. Fields that may be redundant or have no value for clinical research may be removed from the model (e.g., ResultSignedBy) and/or new fields may be added to further clarify the model (e.g., ResultNameCode, which can map to a standard terminology, allowing researchers to use well known standard terminology to analyze data).

With the syntactic normalization process, the health data platform can also leverage AI and machine learning to scan data for certain errors and syntactic inconsistencies such as units of measurement. The system not only corrects measurements to a standard value but also alerts for measurements that fall outside of expected values. For example, a date of birth outside regular syntax might be flagged, as would a weight denoted with a negative number.

Once data has been organized into common fields and normalize syntax, the health data platform can normalize names, values, and/or other data within those fields through semantic normalization.

As with syntactic normalization, the present technology may need to create a normalization model that can standardize terminology while also maintaining as much detail as possible for research. With semantic normalization, the challenge is even more complex. In some embodiments, the model is applied to billions of observations and diagnostic values.

To build this model, leading medical ontologies are selected for each major subject area and practice domain covered in the data. These ontologies can then be combined to create a superset of ontologies in the disclosed model. These categories and related ontologies can include:

Diagnosis

- ICD-10-CM: The International Classification of Diseases and Related Health Problems (ICD) Clinical Modification is used by U.S. physicians and other healthcare providers to classify and code all diagnoses, symptoms, and problems. Like its predecessor ICD-9-CM, ICD-10-CM is published by the National Center for Health Statistics of the U.S. government.
- ICD-10-PCS. The International Classification of Diseases and Related Health Problems (ICD) Procedure Coding System is used for classifying procedures performed in hospital inpatient health care settings.

Supplies and Equipment

- HCPCS. The Healthcare Common Procedure Coding System represents medical procedures, supplies, products, and services.

Lab and Clinical Observations

- LOINC: Logical Observation Identifiers Names and Codes was created specifically to standardize the identification and reporting of medical laboratory observations, including measurements. It has been expanded to standardize clinical observations as well.
- SNOMED CT: The Systematized Nomenclature of Medicine Clinical Terms (US Edition) is used to standardize clinical findings, disorders, body structures, procedures, microorganisms, allergies, and various other clinical domains.

Medications

- NDC. The National Drug Code provides a list of all drugs manufactured or processed for off-the-shelf, commercial distribution.
- CVX. The Vaccine Administered (CVX) standard covers active and inactive vaccine terms for the US.
- RxNorm provides standard names for clinical drugs (active ingredient+strength) and for dose forms.

Figure 3:
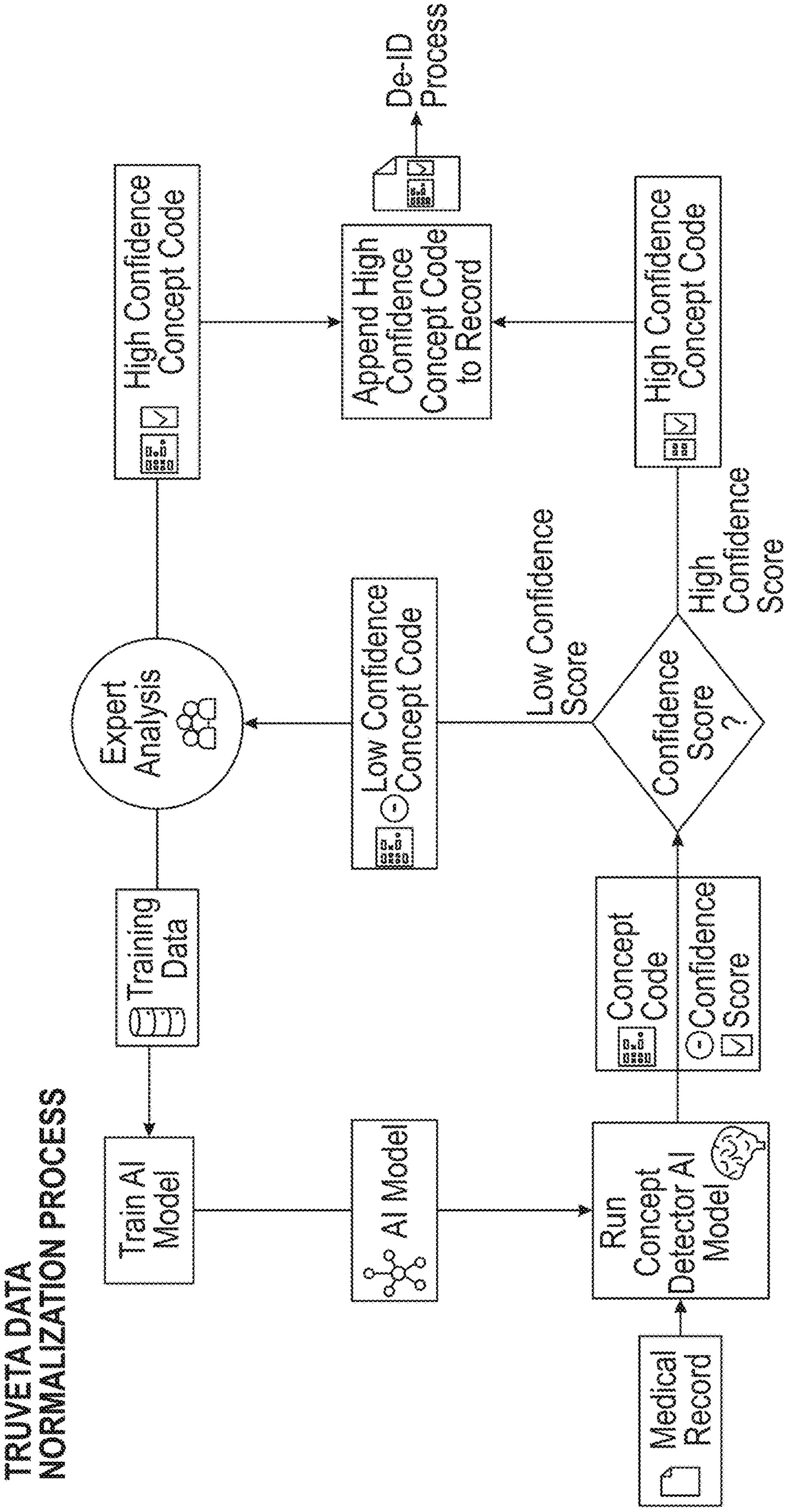
FIG. 3 illustrates a data normalization process, in accordance with embodiments of the present technology.

The system then matches terms in a record to standard terms or "concepts" from the ontologies in the model. This is done through the Concept Detector AI model (FIG. 3). A concept code is generated for each concept along with a related confidence score. This score indicates how closely the model thinks a concept matches the term in the record. In some embodiments, these confidence scores are important to ensuring the accuracy and ongoing evolution of the normalization process.

FIG. 4 illustrates an example in which the system has mapped two diagnoses to two standard SNOMED CT concepts. The system has also generated several confidence scores. These are "high confidence" scores, indicating that the system sees a very close match between the two standard SNOMED concepts and the terms in the record.

With high confidence scores such as these, the related concept codes can be appended to the record and sent through the system for further processing, including de-identification. Concept codes with low confidence scores can take a different path. In these cases, the record and related codes can be sent to a team of annotators and informaticists for review and comparison. The code can be amended, if needed, with a more appropriate concept, added to the record, and sent into the pipeline.

The code can also be used to train AI models. In some embodiments, the training can be done using advanced techniques known as transfer learning-a practice in machine learning that focuses on storing knowledge gained while solving one problem and applying it to a different but related problem.

The system described herein can solve millions of normalization "problems" a day. Using the unique, machine learning models described herein, this can be achieved at ultra-high speed with exceptional accuracy. The result is an effectively normalized data pipeline, ready for research and/or other applications with the very latest data from health system members.

The machine learning system incorporated in the health data platform can be engineered to grow and evolve as quickly as the diversity of the data that it processes. In some embodiments, this includes the use of new and updated ontologies as well as the terms which are added continuously by a team of annotators and informaticists. The result is normalization at a speed and scale unique in the healthcare industry.

Figure 5:
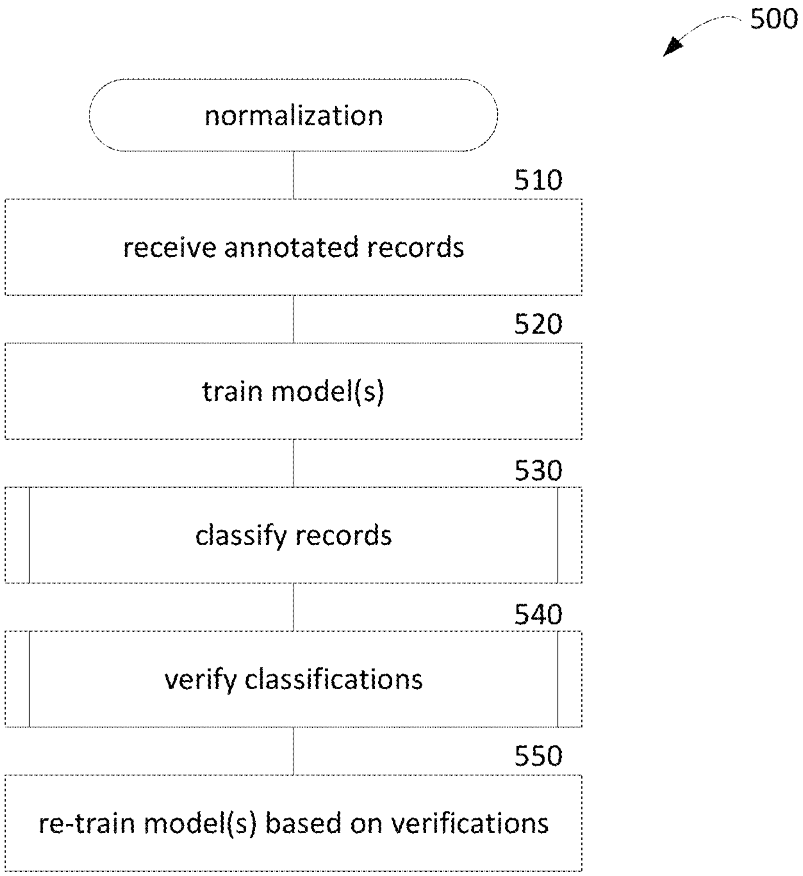
FIG. 5 is a block diagram illustrating processing of a normalization component in accordance with some embodiments of the present technology.

FIG. 5 is a block diagram illustrating processing of a normalization component in accordance with some embodiments of the present technology. In this example, method 500 normalizes one or more records, such as medical records, using one or more machine learning models trained using a set of annotated medical records by appending, to the records, classification information generated using the one or more machine learning models. In block 510, the normalization component receives annotated records, such as annotated medical records, from one or more sources, such as a repository of annotated records, one or more users or experts in the field of annotated records, and so on. For example, the annotated records may include, for each record, an annotation of one or more concepts or codes associated with the medical record, such as one or more classification codes from a medical ontology. In block 520, the component trains one or more models, such as machine learning models, using the annotated records. For example, the component may train one model for classifying records according to one ontology or set of ontologies (and corresponding records annotated in accordance with those ontologies). As another example, the component may train one or more models according to a set of records that have been annotated with syntactic classifications or fields and further train one or more models according to a set of records that have been annotated with semantic classifications or fields. In this manner, the component can train and apply any number of models for any number of classification or normalization purposes. The machine learning models may be any of a variety or combination of models or classifiers including neural networks such as fully-connected, convolutional, recurrent, autoencoder, or restricted Boltzmann machine, a support vector machine, a Bayesian classifier, and so on. When the machine learning model is a deep neural network, the training results in a set of weights for the activation functions of the deep neural network. A support vector machine operates by finding a hyper-surface in the space of possible inputs. The hyper-surface attempts to split the positive examples (e.g., feature vectors for records associated with a particular condition) from the negative examples (e.g., feature vectors for records that are not associated with the particular condition) by maximizing the distance between the nearest of the positive and negative examples to the hyper-surface. This step allows for correct classification of data that is similar to but not identical to the training data. Various techniques can be used to train a support vector machine.

Adaptive boosting is an iterative process that runs multiple tests on a collection of training data. Adaptive boosting transforms a weak learning algorithm (an algorithm that performs at a level only slightly better than chance) into a strong learning algorithm (an algorithm that displays a low error rate). The weak learning algorithm is run on different subsets of the training data. The algorithm concentrates more and more on those examples in which its predecessors tended to show mistakes. The algorithm corrects the errors made by earlier weak learners. The algorithm is adaptive because it adjusts to the error rates of its predecessors. Adaptive boosting combines rough and moderately inaccurate rules of thumb to create a high-performance algorithm. Adaptive boosting combines the results of each separately run test into a single, very accurate classifier. Adaptive boosting may use weak classifiers that are single-split trees with only two leaf nodes.

A neural network model has three major components: architecture, cost function, and search algorithm. The architecture defines the functional form relating the inputs to the outputs (in terms of network topology, unit connectivity, and activation functions). The search in weight space for a set of weights that minimizes the objective function is the training process. In one embodiment, the classification system may use a radial basis function ("RBF") network and a standard gradient descent as the search technique.

In some embodiments, an AI system may use various design-of-experiments ("DOE") techniques to identify values of feature vectors of consumer entities that result in positive outcomes for various action inducers. Suitable DOE techniques include central composite techniques, Box-Behnken techniques, random techniques, Plackett-Burman techniques, Taguchi techniques, Halton, Faure, and Sobel sequences techniques, Latin hypercube techniques, and so on. (See Cavazzuti, M., "Optimization Methods: From Theory to Design," Springer-Verlag Berlin Heidelberg, 2013, chap. 2, pp. 13-56, which is hereby incorporated by reference in its entirety.) The Latin hypercube technique has the characteristic that it generates sample values in which each axis (i.e., feature) has at most value that is selected.

In block 530, the component invokes a classify records component to apply one or more of the trained models to a set of one or more records, such as medical records that have not been classified. In some cases, after classifying records, the component may apply one or more de-identification techniques, such as those described in U.S. Provisional Patent Application No. 63/263,731, entitled "SYSTEMS AND METHODS FOR DE-IDENTIFYING PATIENT DATA," filed on Nov. 8, 2021, which is herein incorporated by reference in its entirety. In block 540, the component invokes a verify classifications component to assess the quality of the classifications performed by the one or more trained models at block 530. In block 550, the component re-trains the one or more models based on the verified classifications. In this manner, the present technology employs active learning techniques to enable the output of each trained model to inform and improve the training of future iterations of a corresponding model. Accordingly, the models employed by the disclosed system can improve over time based on feedback from the training itself. In response to receiving additional records, the newly trained models can be applied to the additional records (e.g., at block 520) to classify the additional records and further improve the underlying models.

Figure 6:
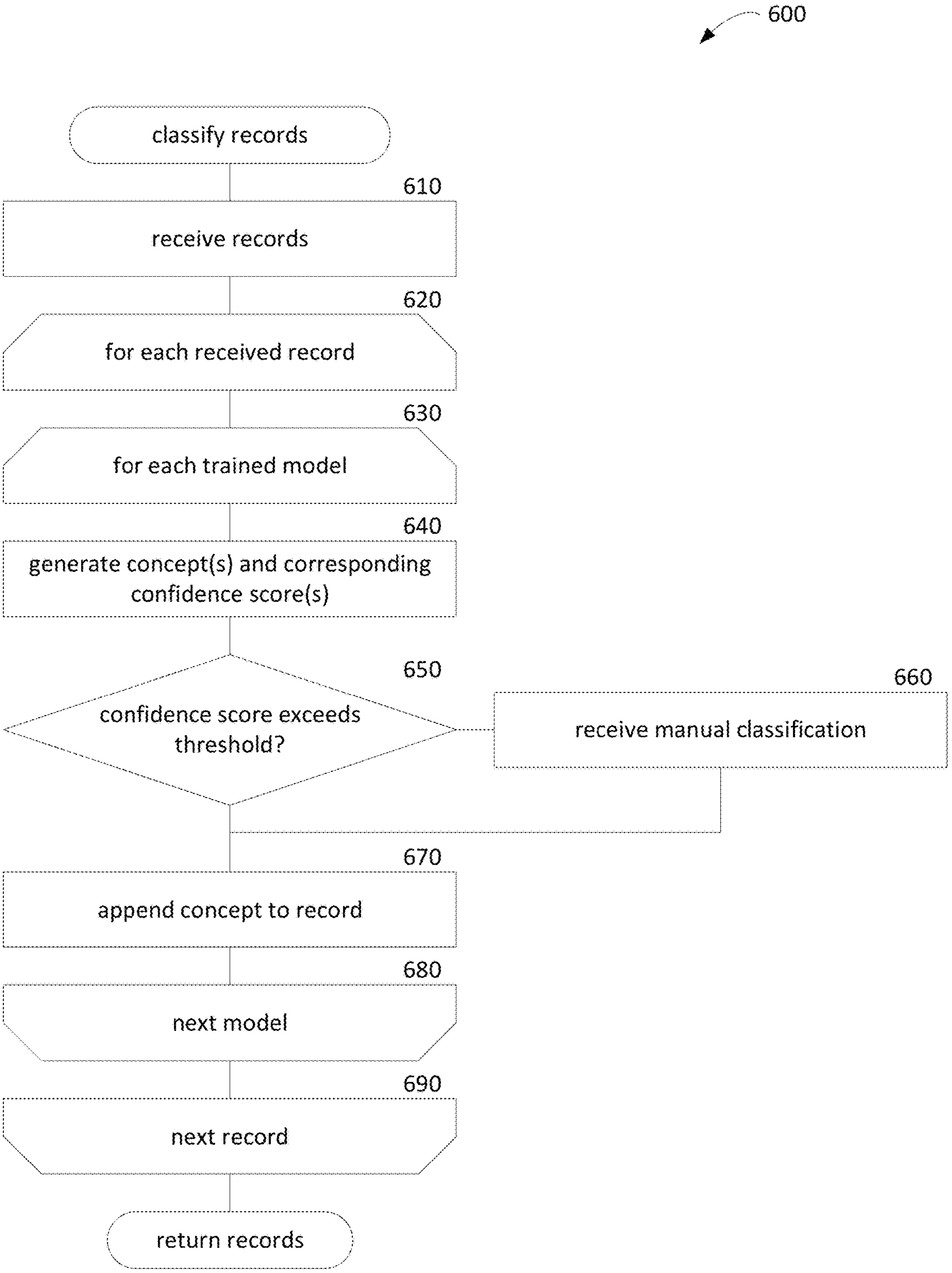
FIG. 6 is a block diagram illustrating processing of a classify records component in accordance with some embodiments of the present technology.

FIG. 6 is a block diagram illustrating processing of a classify records component in accordance with some embodiments of the present technology. In this example, method 600 is invoked by the normalization component and is performed to classify one or more records, such as medical records using one or more models (e.g., machine learning models) trained using a set of annotated medical records. In block 610, the classify records component receives one or more records for classification, such as a set of new or updated medical records. In blocks 620-690, the component loops through each of the records to classify the record according to one or more trained models. In blocks 630-680, the component loops through each of the models to generate concepts and corresponding confidence scores for the currently-selected record. In block 640, the component applies the currently selected trained model to the currently selected record to generate one or more concepts for the record. For example, the component may generate a set of features (feature vector) from the record and apply the model to the feature vector to generate one or more concepts. The component may analyze the record and corresponding metadata to generate one or more values for each of a plurality of attributes, such as patient data attributes, metadata attributes, and so on. For example, the component may apply a metadata transform to one or more records to convert attributes of the records to a feature vector storing values for one or more metadata attributes of the record. Furthermore, the model can specify a confidence score (e.g., 0.1, 0.5, 0.95, 0.99, 1.0) for each generated concept indicating the likelihood that the generated concept is represented in the record. In this manner, each record can be classified according to one or more concepts. In decision block 650, if the confidence score for a particular concept is greater than a threshold (e.g., 0.5, 0.8, 0.95, 0.9875), then the component continues at block 670, else the component continues at block 660. In block 660, the component sends the record to a user or expert for manual classification. In some cases, the component may wait until all concepts have been generated for a particular record before sending the record and corresponding data for manual classification. In some cases, the component may include with the record a list or ranked list of concepts generated for the record. For example, the list of concepts may be ranked according to their corresponding confidences scores. As another example, the concepts may be ranked at a first level based on an accuracy score associated with the model that generated each concept and then ranked according to the confidences scores. In block 670, the component adds the concepts whose confidence scores exceed the threshold (and any manual classifications) to the record. In this manner, the record has been classified and "normalized" using a model trained in accordance with a number of annotated records, such as records annotated according to one or more ontologies. In block 680, if there are any trained models remaining, then the component selects the next trained model and loops back to block 640 to generate one or more concepts and corresponding to confidence scores for the currently selected record using the newly selected model, otherwise the component continues at block 690. In block 690, if there are any records remaining, then the component selects the next record and loops back to block 630 to apply the trained models to the newly selected record, otherwise the component returns an indication of the records to the normalization component. Although described as classifying records according to different concepts, one of ordinary skill in the art will recognize that the trained models may be configured to classify records according to any number of attributes.

Figure 7:
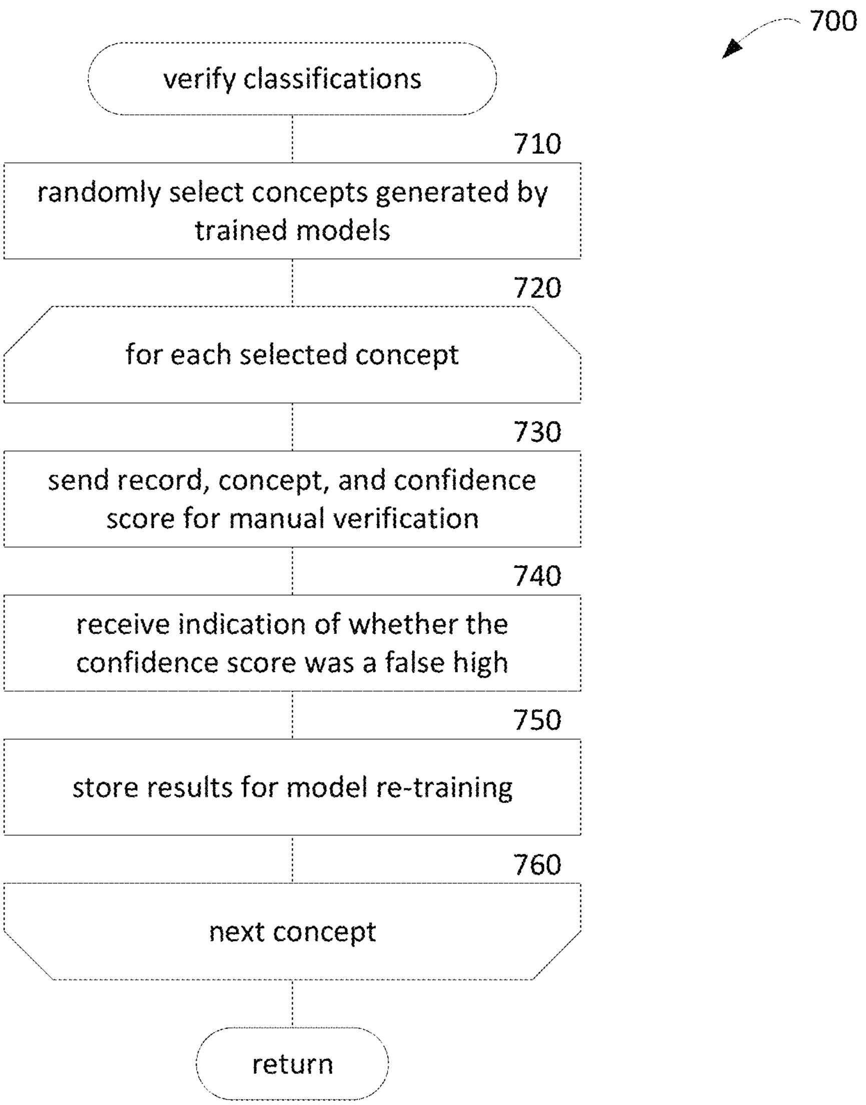
FIG. 7 is a block diagram illustrating processing of a verify classifications component in accordance with some embodiments of the present technology.

FIG. 7 is a block diagram illustrating processing of a verify classifications component in accordance with some embodiments of the present technology. In this example, method 700 is invoked by the normalization component and is performed to verify the accuracy of classifications (e.g., concepts) assigned to records and corresponding confidence scores. In block 710, the component randomly selects concepts generated by the trained models. For example, each time a trained model classifies a record (e.g., generates a concept for a record) with a confidence score that exceeds a predetermined threshold (e.g., 0.5, 0.96, 0.995), the component may generate a random number (e.g., between 0.0 and 1.0) for the concept and if the generated number exceeds a predetermined threshold (e.g., 0.1., 0.5, 0.75), then the concept (and corresponding record/confidence score) can be flagged for verification purposes. In this manner, the randomly selected concepts can be marked for verification, which may occur periodically. One of ordinary skill in the art will recognize that other methods for randomly selecting classifications (e.g., concepts) for verification may be employed. In blocks 720-760, the component loops through each of the randomly selected concepts to assess their quality. In block 730, the components sends an indication (e.g., link or reference) of the currently selected concept and corresponding record and confidence score to a user for a manual assessment. The user, in turn, can analyze the record to determine whether the concept is, in fact, represented in the record. In block 740, the component receives, from the user, an indication of whether the confidence score for the concept was a false high. For example, if the concept was attributed to the record by a trained model but is not represented in the record (according to the user), then the confidence score was a false high). In some cases, the component may request manual assessment from multiple users. In block 750, the component stores the results for use in training subsequent generations of the models. In this manner, the output of each trained model can be used to inform and improve the training of future iterations of the model. Accordingly, the models employed by the disclosed system can improve over time based on feedback from the training itself.

The methods illustrated in FIGS. 5-7 can be modified in many different ways. For example, some or all of the steps of the methods 500, 600, and 700 can be repeated. In some embodiments, the health system provides a dynamic stream or feed of patient records to the health data platform, which may include records for new patients as well as updated records for existing patients. Accordingly, the methods can be repeated (e.g., continuously, at predetermined intervals, when new data is available) to normalize the additional records. Optionally, one or more of the steps of the methods can be omitted (e.g., the suppression process of block 540) and/or the methods can include additional steps not shown. As another example, method 500 may be modified to include one or more additional blocks, such as one or more blocks for automatically generating and transmitting messages to one or more users, such as a health care professional or patient. For example, in response to the health data platform receiving or acquiring new and/or updated records, the health data platform can normalize the new and/or updated records, automatically generate a message containing the new and/or updated records whenever new and/or updated records are received or stored, and transmit the automatically generated message to one or more users over a network in real time, so that those users have immediate access to the new and/or updated patient records.

III. Metadata Driven Normalization

In some embodiments, the present technology employs metadata driven normalization techniques to further enhance and speed up the normalization process. As discussed above, the task of interpreting health data and mapping to standard models is conventionally done by an expert team of annotators, informaticists, clinical experts, and so on. Using the disclosed metadata driven normalization (or "configuration driven normalization") process, rather than directly writing instructions that execute transformations from one data format to another, system operators can provide "configurations" that the disclosed systems use to automatically generate and execute code for normalizing or transforming data. In this manner, the user need not be familiar with a target format or data structure in order to convert a record set to the target format or data structure. Rather, the references to instructions can be used to invoke the necessary instructions to generate code to transform the data. These techniques considerably reduce the time and effort needed to onboard new data sources, such as data from a new hospital system that may have a proprietary schema, or enabling new mode of data such as genomics. Furthermore, these techniques reduce the time needed to integrate and analyze data for use.

The metadata driven normalization process provides significant improvements over conventional normalization processes. For example, because the transformation code is generated automatically, it is less susceptible to user error and intermittent user "customizations" that may be inconsistent with an ontology or structure of, for example, a master data catalog or other standardized format. Moreover, these processes provide for consistent validation when ingesting new data into a pre-existing system. Moreover, because the data modelers, analysts, etc. are not responsible for transforming or generating code to do so, they can operate independent of any known or unknown target data platform.

The disclosed techniques provide methods and systems for metadata driven normalization processes. In some examples, the metadata data normalization process includes receiving a number of configuration data structures (e.g., files) that each map a source format (e.g., a propriety format for storing data) or portion thereof to a target format (e.g., a standardized format for storing data) or portion thereof via referenced instructions or code that can be executed to convert data from the source format to the target format. Each configuration data structure further identifies metadata values associated with the source format, such as labels used to identify data fields in the source format, the provider of the data in the source format, when the source format was first generated, chronological information about when the source format was in use, version information for the source format, and so on.

As discussed above with reference to FIG. 2, different data providers may each use different formats to store data that represents the same type of information (e.g., relational, graph data model, document, messages, etc.). Furthermore, each of these formats may be different than a target standardized format. In the example seen in FIG. 2, there are three different labels for data corresponding to a unit of measure, the three labels including "Unit," UnitOfMeasure," and "UOM." In this example, the label for this field in the target format is "UnitOfMeasure" whereas the label in a source format for an entity labeled "HS1" is "Unit" and the label in a source format for an entity labeled "HS2" is "UOM." Accordingly, a configuration data structure for mapping the HS1 source format to the target format could include a reference to code for replacing "Unit" with "UnitOfMeasure" or a reference to general code for renaming labels that can be passed one or more parameters to fit a specific transformation. Similarly, a configuration data structure for mapping the HS2 source format to the target format could include a reference to code for replacing "UoM" with "UnitOfMeasure." One of ordinary skill in the art will recognize that a source format may become a target format and vice versa. Thus, although in the example of FIG. 2 the HS1 and HS2 format each corresponds to a source format, configuration data structures could be generated to transform the target format into either of these formats and/or to convert one of these source formats into the other. In some cases, this transformation may include a number of intermediate transformations, such as a transformation from the HS1 source format to the target format in FIG. 2 and then from that target format to the HS2 format (in this example the HS2 format is the target format).

In some examples, the configuration data structures may also include mappings to instructions for transforming how underlying data is stored. For example, a source format may store date and time information in a single field whereas the same information is stored in separate fields in a target format, such as a separate field for date and a separate field for time or separate fields for each of year, month, date, and time. Accordingly, a configuration data structure for converting from the source format to the target format could include a reference to code for separating date and time entries into individual fields. Conversely, a configuration data structure for converting from the target format to the source format could include a reference to code for merging date and time entries into a single field.

In some examples, the configuration data structures may also include mappings to instructions for transforming for changing values of underlying data to be consistent with a target format. For example, a source format may store data using the metric system (e.g., kilograms) while the same information is stored using the imperial system (pounds) in a target format. Accordingly, a configuration data structure for converting from the source format to the target format could include a reference to instructions for converting from one system to the other (e.g., kilograms to pounds).

When new data is received, the metadata normalization process can analyze metadata associated with the new data and compare the metadata to metadata associated with various stored configuration data structures to produce scores for the configuration data structures. For example, the metadata normalization process can compare data field labels associated with each to determine how many "match" (i.e., are identical or within a predetermined distance (e.g., Levenshtein distance) from each other, compare source information, compare timing or version information, and so on. For each metadata value identified in the new set of records, the process can generate a difference value. Once these difference values are generated an overall distance can be generated based these differences, such as a Euclidean distance, and so on. In some cases, different metadata values may be weighted differently than others. For example, configuration data structures that are associated with the same source (e.g., hospital) as the new data may receive higher scores than configuration data structures associated with different sources. Similarly, configuration data structures with the same source and version number may be ranked higher than configuration data structures associated with the same source but that have a different version number, etc. In some cases, configuration data structures may each include a unique identifier that can be included with incoming data to ensure that a desired configuration data structure is invoked to transform the incoming data. In this manner, multiple configuration data structures can be identified that each transform different portions of retrieved data.

After scores are generated for the configuration data structures, the highest scoring configuration data structure is selected, and corresponding or referenced instructions are retrieved and used to generate code that can then be applied to the incoming data to transform the incoming data from its source format to a target format. For example, the configuration data structure may include references to instructions for converting tabular data field labels (i.e., renaming), instructions for merging or separating columns in tabular data, instructions for transforming tabular data into a relational database (e.g., instructions for adding data fields to the appropriate tables and instructions for inserting foreign and primary keys to maintain links between data for individual records, and so on). After applying the transformation instructions, the transformed data can be stored or merged with another data source. In this manner, the incoming data has been normalized without a user having to analyze the incoming data, thereby reducing the amount of time required to integrate the incoming data with one or more sources and freeing up resources for other applications.

In some examples, the metadata data normalization process perform various data quality checks during the transformation process. For example, a configuration data structure and/or target format may define limits or requirements on various data fields, such as minimum values, maximum values, eligible values, and so on. Thus, if one or more values being input is not consistent with these restrictions (i.e., is invalid) these values can be flagged for review or discarded altogether. As another example, if a value being entered is inconsistent with statistical information for a particular data field (e.g., more than a predetermined number of standard deviations from a mean value), the value can be flagged for review. In this manner, the metadata normalization process can provide metrics and alerts related to data quality, thereby improving the quality of incoming and normalized data.

One of ordinary skill in the art will recognize that data may be converted or normalized to any number of formats, such as formats for storing data, formats for sending data, formats for analyzing data, and so on. For example, various models or entities may require or prefer that data be formatted in a particular way. The techniques described herein may be used to convert or normalize data for any number of data formats and through any number of sequence of formats. Accordingly, even if a configuration data structure for converting data directly from a first format to a second format, the conversion may still be available through the use of configuration data structures used to convert the data through a series of intermittent data formats. One of ordinary skill in the art will recognize that data can be formatted to and from data formats for relational data sources (e.g., databases), document sources (e.g., PDF, MS Word), message formats (e.g., SMS, email), data modeling formats (e.g., neural networks, feature vectors), XML formats, hierarchical formats (e.g., json, protobuff, CDA), graph data models, proprietary formats, and so on and/or various versions of any of these data formats.

Figure 8:
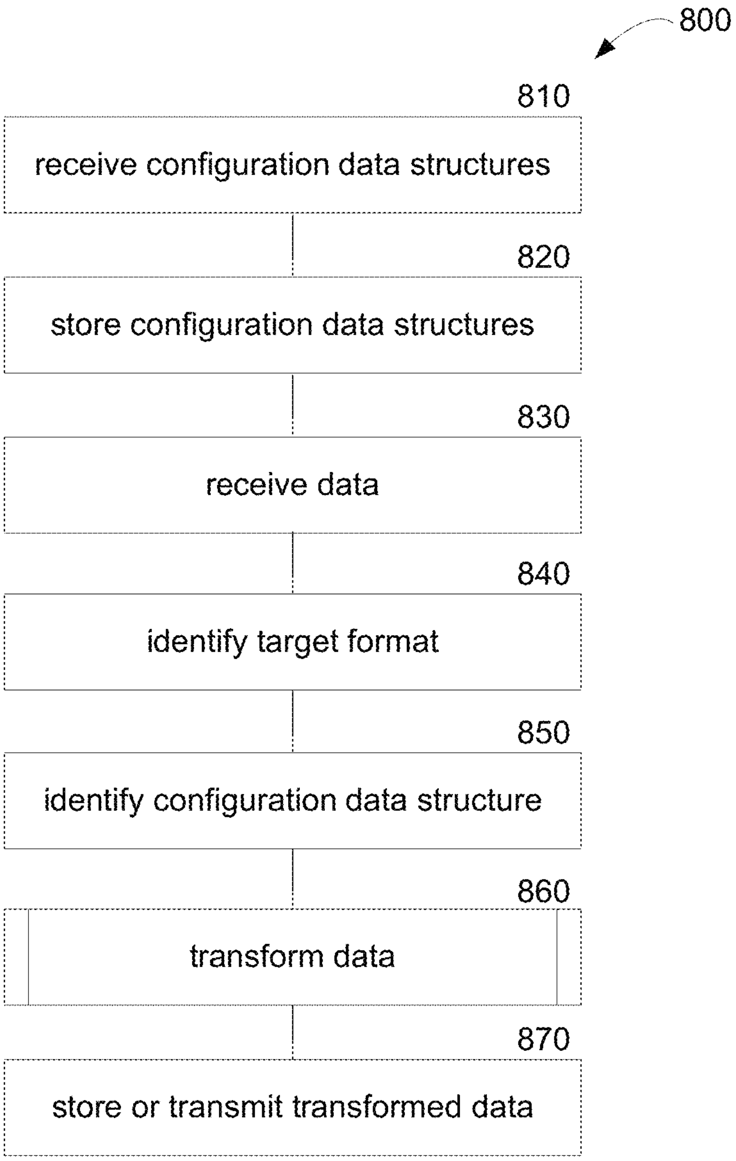
FIG. 8 is a flow diagram illustrating the processing of a metadata normalization component in accordance with some embodiments of the disclosed technology.

FIG. 8 is a flow diagram illustrating the processing of a metadata normalization component in accordance with some embodiments of the disclosed technology. In block 810, the component receives configuration data structures, each configuration data structure identifying a source format, a target format, and referenced instructions for transforming data from the source format to the target format. In some examples, the configuration data structures may also include metadata information pertaining to the formats, such as a provider of the formats, version information for the formats, chronological information pertaining to the formats, data field labels associated with the formats, schema or other structural information associated with the formats, and so on. In block 820, the component stores the configuration data structures in, for example, in a common data store or a separate configuration data structure store. In block 830, the component receives data, such as an updated set of records from a data provider, a set of records from a new data provider, a subset of previously stored records included in a request to format the data, etc. The new data can include metadata, such as metadata identifying a source of the data, a format and/or format version for the data, data field labels, etc. In block 840, the component identifies a target format, such as a standardized format, a format identified in a request to transform the data, a format identified for a user, etc.

In block 850, the component identifies a configuration data structure to transform the received data from the source format to the target format. In some examples, the received data uniquely identifies a configuration data structure or a source format and a target format. In these cases, the component can identify a corresponding data structure (i.e., the uniquely identified configuration data structure or a configuration data structure that identifies the source and target formats). If no such configuration data structure is available, the component may alert a user so that a request to generate or retrieve such a configuration data structure can be transmitted. In some examples, the component may determine whether there exists a chain of configuration data structures that can be used, in sequence, to transform the received data to the target format. In some examples, the component identifies a configuration data structure by comparing metadata associated with the new data to metadata information associated with each of a plurality of configuration data structures, such as configuration data structures received in block 810 and/or previously received and stored configuration data structures and scores the configuration data structures. For example, the component can identify data field labels in the received data to determine how many "match" any data field labels identified in the configuration data structures. In some examples, the component may first filter the configuration data structures to include only configuration data structures that match one or more metadata elements of the received data prior to scoring the configuration data structures.

In block 860, the component invokes a transform data component discussed in further detail below with respect to FIG. 9 to transform the data to the target format. In block 870, the component stores or transmits the transformed data. For example, the component may store the transformed data in a data repository storing data in the target format, transmit the transformed data to a user or process that sent a request to transmit the data, and so on. In some cases, the component may loop back to block 840 to identify a new target format for the transformed data if, for example, the component is being invoked as part of a sequential format transformation from an original source format to a final target format.

Figure 9:
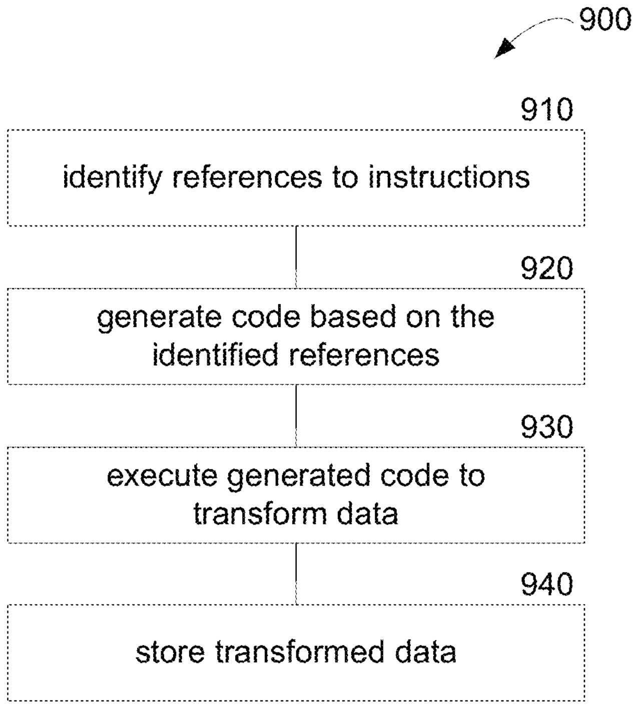
FIG. 9 is a flow diagram illustrating the processing of a transform data component in accordance with some embodiments of the disclosed technology.

FIG. 9 is a flow diagram illustrating the processing of a transform data component in accordance with some embodiments of the disclosed technology. The transform data component is invoked to apply one or more configuration data structures to a data set to transform the data set from a source format to a target format. In block 910, the component identifies references to instructions in the configuration data structure(s). In block 920, the component generates code for each of the identified references to instructions. For example, the component may retrieve source code for transforming data from one format to another, input identifiers for one or more elements of the input data into the source code, then compile and execute the source code to transform the data. A reference may link to code for renaming a data field label from a given input or source label to a given output or target label. The component can retrieve this source code and replace placeholders in the source code with given labels (e.g., "UOM" for a source label and "UnitOfMeasure" for a target label) and then compile and execute the code to replace the "UOM" label with "UnitOfMeasure." As another example, a reference may link to code for merging columns in a source format and naming the merged column using a given label (e.g., column1, column2, column3, "date"). In this example, the component can generate code by replacing placeholders in the code for column names with the known column names (e.g., "year," "month," "day") and a placeholder for the name of the new column (e.g., "date"). This generated code can then be compiled and executed to merge the cells and name the merged cell. In some examples, the component may invoke local or remote instructions directly by passing input parameters to the referenced instructions, without having to compile generated code. One of ordinary skill in the art will understand that these functions and/or procedures may be invoked locally or remotely using any number of procedure calling techniques and/or through the use of linked libraries, and so on. In block 930 the component executes the transformation code, such as newly compiled code or previously compiled code. Executing these instructions transforms the input data to the target data, which can then be stored or transmitted for additional use.

The methods 800 and 900 illustrated in FIGS. 8 and 9 can be modified in many different ways. For example, some or all of the steps of the methods 800 and 900 can be repeated. In some embodiments, the health data platform receives a feed of patient records from outside parties, which may include records for new patients as well as updated records for existing patients. Accordingly, the processes of blocks 810-870 and 910-940 of the methods 800 and 900 can be repeated (e.g., continuously, at predetermined intervals, when new data is available) to process and aggregate additional records from the same data provider. As another example, the processes of blocks 810-870 and 910-940 of the methods 800 and 900 can be repeated for multiple parties to transform data for each party. Optionally, one or more of the steps of the methods 800 and 900 can be omitted and/or the methods 800 and 900 can include additional steps not shown in FIGS. 8 and 9.

Figure 10:
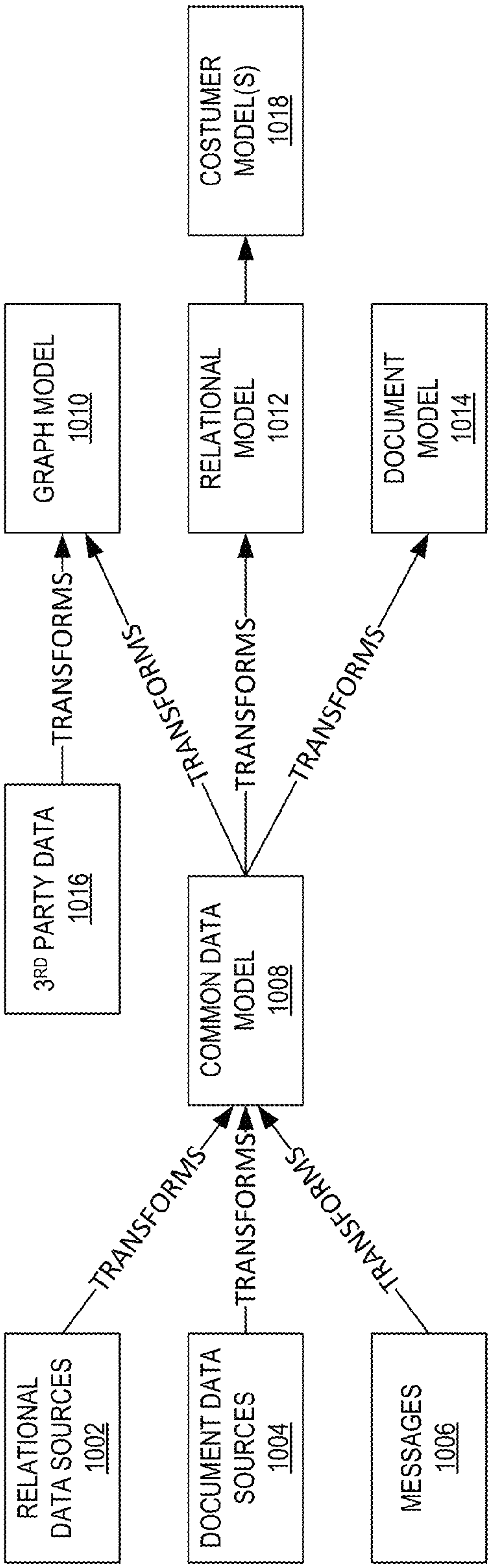
FIG. 10 illustrates an example data flow involving metadata driven normalization in accordance with some embodiments of the disclosed technology.

FIG. 10 illustrates an example data flow involving metadata driven normalization in accordance with some embodiments of the disclosed technology. As illustrated, a plurality of different data sources (relational data sources 1002, document data sources 1004, and messages 1006) can each be transformed to a common data model 1008. As described above, this transformation can involve applying one or more configuration data structures to transform the data set from the source format (e.g., a format associated with the relational data sources 1002) to a target format (e.g., a format associated with the common data model). This common data model 1008 can facilitate analysis and evaluation of a combined data set that draws from many different sources. Moreover, data (all or a desired subset of the data) can be output to various target models via additional transformations (e.g., output to a graph model 1010, a relational model 1012, or a document model 1014). In some implementations, 3rd party data 1016 can additionally be combined with data from the common data model 1008 to produce the target output model (e.g., the graph model 1010). In the illustrated example, one or more customer-specific models 1018 can be output using the relational model 1012. The diagram shown in FIG. 10 illustrates one simplified example of possible transformations enabled by the metadata driven normalization techniques described herein. In various implementations, the particular number and type of data sources and output models can vary. In at least some examples, there may be no intervening common data model 1008, and instead a given data source type can be transformed directly into a desired output model type (e.g., document data sources 1004 transformed to be output to graph model 1010).

CONCLUSION

Although many of the embodiments are described above with respect to systems, devices, and methods for processing patient data and/or other health data, the technology is applicable to other applications and/or other approaches. For example, the present technology can be used in other contexts where data privacy is an important consideration, such as financial records, educational records, political information, location data, and/or other sensitive personal information. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-10.

The various processes described herein can be partially or fully implemented using program code including instructions executable by one or more processors of a computing system for implementing specific logical functions or steps in the process. The program code can be stored on any type of computer-readable medium, such as a storage device or storage medium, which includes, for example, a disk or hard drive but does not include transitory computer-readable media. Computer-readable media containing code, or portions of code, can include any appropriate media known in the art, such as non-transitory computer-readable storage media. Computer-readable media can include volatile and non-volatile, removable and non-removable media implemented in any method or technology for storage and/or transmission of information, including, but not limited to, random-access memory (RAM), read-only memory (ROM), electrically erasable programmable read-only memory (EEPROM), flash memory, or other memory technology; compact disc read-only memory (CD-ROM), digital video disc (DVD), or other optical storage; magnetic cassettes, magnetic tape, magnetic disk storage, or other magnetic storage devices; solid state drives (SSD) or other solid state storage devices; or any other medium which can be used to store the desired information and which can be accessed by a system device.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A computer-readable storage medium storing instructions that, when executed by a computing system having a memory and a processor, cause the computing system to perform a method for normalizing data, the method comprising:

receiving a first configuration data structure comprising one or more mappings, each mapping comprising a reference to instructions for transforming data from a first format into a standardized format;

receiving a second configuration data structure comprising one or more mappings, each mapping comprising a reference to instructions for transforming data from a second format into the standardized format;

receiving a first data set, the first data set including at least one value for each of a first plurality of data fields;

receiving a second data set, the second data set including at least one value for each of a second plurality of data fields; and for each of the received data sets, identifying a configuration data structure to use to transform the received data set, wherein the identifying comprises:

identifying metadata associated with the received data set, generating a score for the first configuration data set based on the identified metadata associated with the received data set and metadata values associated with the first format, generating a score for the second configuration data set based on the identified metadata associated with the received data set and metadata values associated with the second format, in response to determining that the score generated for the first configuration data structure is greater than the score generated for the second configuration data structure, identifying the first configuration data structure to use to transform the received data set, and in response to determining that the score generated for the first configuration data structure is less than or equal to the score generated for the second configuration data structure, identifying the second configuration data structure to use to transform the received data set, generating instructions for transforming the received data set into the standardized format, wherein generating the instructions for transforming the received data set into the standardized format comprises retrieving, based on at least one mapping of the identified configuration data structure, instructions for transforming data into the standardized format, transforming the received data set into the standardized format by applying the generated instructions to the received data set, and storing the transformed data set.

2. The computer-readable storage medium of claim 1, wherein each of the received data sets comprises health records.

3. The computer-readable storage medium of claim 1, the method further comprising:

for each of a plurality of configuration data structures, each configuration data structure identifying metadata values associated with a source format of the configuration data structure, comparing the metadata associated with each received data set to the metadata values associated with the source format of the configuration data structure.

4. The computer-readable storage medium of claim 3, wherein identifying metadata associated with each received data set comprises identifying one or more data field labels, a unique identifier for a source of the received data set, and a version number.

5. The computer-readable storage medium of claim 1, wherein the first configuration data structure comprises a reference to instructions for transforming a first portion of a data set received from a first source from the first format into the standardized format and the second configuration data structure comprises a reference to instructions for transforming a second portion of the data set received from the first source from the first format into the standardized format.

6. The computer-readable storage medium of claim 1, wherein at least one of the one or more mappings comprises a reference to source code for merging one or more columns into a single column in the standardized format.

7. A computing system for normalizing data, the computing system comprising:

at least one processor; and at least one memory storing instructions that, when executed by the computing system, cause the computing system to perform operations comprising:

receiving a first configuration data structure comprising one or more mappings, each mapping comprising a reference to instructions for transforming data from a first format to a standardized format, receiving a second configuration data structure comprising one or more mappings, each mapping comprising a reference to instructions for transforming data from a second format to the standardized format, receiving a first data set, the first data set including at least one value for each of a first plurality of data fields, receiving a second data set, the second data set including at least one value for each of a second plurality of data fields, for each of the received data sets, identifying a configuration data structure to use to transform the received data set, wherein the identifying comprises:

identifying metadata associated with the received data set, generating a score for the first configuration data set based on the identified metadata associated with the received data and metadata values associated with the first format, generating a score for the second configuration data set based on the identified metadata associated with the received data and metadata values associated with the second format, in response to determining that the score generated for the first configuration data structure is greater than the score generated for the second configuration data structure, identifying the first configuration data structure to use to transform the received data set, and in response to determining that the score generated for the first configuration data structure is less than or equal to the score generated for the second configuration data structure, identifying the second configuration data structure to use to transform the received data set, and generating instructions for transforming the received data set into the standardized format, wherein generating the instructions for transforming the received data set into the standardized format comprises retrieving, based on at least one mapping of the identified configuration data structure, instructions for transforming data into the standardized format, and transforming the received data set into the standardized format by applying the generated instructions to the received data set.

8. The computing system of claim 7, wherein at least one mapping comprises a reference to instructions for transforming data from the standardized format into a target format.

9. The computing system of claim 7, wherein each configuration data structures identifies a source format and a target format.

10. The computing system of claim 9, the operations further comprising:

identifying a series of configuration data structures for transforming data from the first format to another format via one or more intermediate formats, wherein the identifying is based on the source format and target format identified by each of the one or more configuration data structures.

11. The computing system of claim 9, the operations further comprising:

receiving, from a remote user, at least one updated record in a format other than the standardized format, wherein the format other than the standardized format is dependent on hardware and software platform used by the remote user;

identifying a configuration data structure for converting the at least one updated record into the standardized format; and transforming the at least one updated record into the standardized format using the identified configuration data structure for converting the at least one updated record into the standardized format.

12. A method, performed by a computing system having a memory and a processor, for normalizing data, the method comprising:

receiving a first configuration data structure comprising one or more mappings, each mapping comprising a reference to instructions for transforming data from a first format into a standardized format;

receiving a second configuration data structure comprising one or more mappings, each mapping comprising a reference to instructions for transforming data from a second format into the standardized format;

receiving a first data set, the first data set including at least one value for each of a first plurality of data fields;

receiving a second data set, the second data set including at least one value for each of a second plurality of data fields; and for each of the received data sets, identifying a configuration data structure to use to transform the received data set, wherein the identifying comprises:

identifying metadata associated with the received data set, generating a score for the first configuration data set based on the identified metadata associated with the received data set and metadata values associated with the first format, generating a score for the second configuration data set based on the identified metadata associated with the received data set and metadata values associated with the second format, in response to determining that the score generated for the first configuration data structure is greater than the score generated for the second configuration data structure, identifying the first configuration data structure to use to transform the received data set, and in response to determining that the score generated for the first configuration data structure is less than or equal to the score generated for the second configuration data structure, identifying the second configuration data structure to use to transform the received data set, generating instructions for transforming the received data set into the standardized format, wherein generating the instructions for transforming the received data set into the standardized format comprises retrieving, based on at least one mapping of the identified configuration data structure, instructions for transforming data into the standardized format, transforming the received data set into the standardized format by applying the generated instructions to the received data set, and storing the transformed data set.

13. The method of claim 12, further comprising:

identifying a third configuration data structure for transforming data from the standardized format to a target format; and applying the identified third configuration data structure to a transformed data set to generate a transformed data set in the target format.

14. The method of claim 13, wherein the metadata values associated with the first format include one or more data field labels, a unique identifier for a first source, and a version number.

15. The method of claim 12, wherein the first configuration data structure includes a unique identifier for the first configuration data structure.

16. The method of claim 12, wherein at least one of the mappings comprises a reference to source code for renaming one or more data field labels and wherein at least one of the mappings comprises a reference to source code for converting data from a first unit of measurement to a second unit of measurement.

17. The method of claim 12, wherein generating the score for the first configuration data structure and the first data set comprises calculating, for each of a plurality of metadata values associated with a first format, a distance between the metadata value associated with the first format and a metadata value associated with the first data set.

18. The method of claim 12, further comprising:

receiving, from a first remote user, at least one updated record in a format other than the standardized format, wherein the format other than the standardized format is dependent on hardware and software platform used by the first remote user;

converting the at least one updated record into the standardized format;

generating a set of at least one normalized record from the at least one updated record;

storing the generated set of at least one normalized record;

after storing the generated set of at least one normalized record, generating a message containing the generated set of at least one normalized record; and transmitting the message to one or more users over a network in real time.

19. The method of claim 12, further comprising:

after identifying the first configuration data structure to use to transform the first data set, retrieving, based on the one or more mappings of the first configuration data structure, source code for transforming data from a first format into the standardized format, replacing each of one or more placeholders in the retrieved source code with a corresponding label to produce modified source code; code and compiling the modified source code, wherein transforming the first data set into the standardized format comprises executing the compiled modified source code.

* * * * *